US010858303B1

(12) United States Patent
Ferraro et al.

(10) Patent No.: US 10,858,303 B1
(45) Date of Patent: Dec. 8, 2020

(54) CANNABIDIOL ISOLATE PRODUCTION SYSTEMS AND METHODS

(71) Applicant: Heinkel Filtering Systems, Inc., Swedesboro, NJ (US)

(72) Inventors: Alan Ferraro, Swedesboro, NJ (US); Bob Edwards, Swedesboro, NJ (US)

(73) Assignee: Heinkel Filtering Systems, Inc., Swedesboro, NJ (US)

( * ) Notice: Subject to any disclaimer, the term of this patent is extended or adjusted under 35 U.S.C. 154(b) by 0 days.

(21) Appl. No.: 16/668,432

(22) Filed: Oct. 30, 2019

(51) Int. Cl.
*C07C 37/68* (2006.01)
*C07C 37/70* (2006.01)
*C07C 37/82* (2006.01)
*C07C 37/84* (2006.01)
*F26B 11/14* (2006.01)
*C07C 39/08* (2006.01)
*B01D 29/075* (2006.01)

(52) U.S. Cl.
CPC ............ *C07C 37/68* (2013.01); *C07C 37/685* (2013.01); *C07C 37/70* (2013.01); *C07C 37/82* (2013.01); *C07C 37/84* (2013.01); *F26B 11/14* (2013.01); *B01D 2029/075* (2013.01); *C07C 39/08* (2013.01)

(58) Field of Classification Search
None
See application file for complete search history.

(56) References Cited

U.S. PATENT DOCUMENTS

| | | | |
|---|---|---|---|
| 3,973,984 A | 8/1976 | Hentschel | |
| 5,195,939 A | 3/1993 | Gingras | |
| 5,591,340 A | 1/1997 | Meikrantz | |
| 6,059,712 A | 5/2000 | Corlett | |
| 7,384,557 B2 | 6/2008 | Phillips | |
| 8,728,215 B2 | 5/2014 | Manning | |
| 8,895,078 B2 | 11/2014 | Mueller | |
| 8,998,789 B2 | 4/2015 | Toi | |
| 9,732,009 B2 | 8/2017 | Raber | |
| 9,808,494 B2 | 11/2017 | Barringer | |
| 9,950,976 B1 | 4/2018 | Keller | |
| 10,406,453 B2 | 9/2019 | Ko | |

(Continued)

FOREIGN PATENT DOCUMENTS

CN 101972715 A 2/2011
CN 204111719 U 1/2015

(Continued)

OTHER PUBLICATIONS

Venture ("Marijuana Venture" Journal of Professional Cannabis Growers and Retailers, Published Jan. 16, 2017, pp. 1-54) (Year: 2017).*

(Continued)

*Primary Examiner* — Medhanit W Bahta

(57) ABSTRACT

The disclosure includes systems and methods of producing cannabidiol (CBD) isolate. In some embodiments, a method includes dissolving, via an agitated vessel, CBD oil in a solvent to thereby form a slurry comprising CBD isolate and excess solvent, and sending at least a portion of the slurry from the agitated vessel to an agitated Nutsche filter dryer. Some embodiments include pressurizing an internal portion of the agitated Nutsche filter dryer to remove the excess solvent and capture the CBD isolate in a filter of the agitated Nutsche filter dryer.

21 Claims, 17 Drawing Sheets

(56) References Cited

U.S. PATENT DOCUMENTS

| | | | |
|---|---|---|---|
| 2005/0019438 | A1 | 1/2005 | Bourges-Sevenier |
| 2011/0003888 | A1 | 1/2011 | Kuhrts |
| 2011/0263030 | A1 | 10/2011 | Kim |
| 2013/0079531 | A1 | 3/2013 | Barringer |
| 2015/0126754 | A1 | 5/2015 | Cid |
| 2015/0353865 | A1 | 12/2015 | Poon |
| 2017/0080422 | A1 | 3/2017 | Maaskant |
| 2017/0106030 | A1 | 4/2017 | Aari |
| 2018/0147247 | A1 | 5/2018 | Ivanov |

FOREIGN PATENT DOCUMENTS

| | | |
|---|---|---|
| CN | 105535111 A | 5/2016 |
| CN | 106011207 A | 10/2016 |

OTHER PUBLICATIONS

Salem (How to crystallize CBD—Make CBD isolate, Published Mar. 13, 2019) (Year: 2019).*
Comber ("Nutsche filter or filter dryer", Published Jun. 11, 2019, pp. 1-3) (Year: 2019).*
Heinkel ("Pressofiltro Nutsche Filter/ Filter Dryer", Published Jun. 11, 2019, pp. 1-2) (Year: 2019).*
Alibaba ("Hisen Top Sales CBD Distillate Isolation Agitated Nutsche Filter" Aug. 21, 2018; pp. 1-12) (Year: 2018).*
Comber II (Screen captures from YouTube video clip entitled "Agitated Nutsche filter or filter dryer" 5 pages, uploaded on Apr. 29, 2015 by user "HEINKEL Drying and Separation Group". Retrieved from Internet: < https://www.youtube.com/watch?v=zbS6bX-T3dw>) (Year: 2015).*
Delta Separations; Centrifuge Utility Platform; Downloaded on Jan. 8, 2019 from https://www.deltaseparations.com/extraction/.
Rousselet Robatel; Cannabis Refining; Downloaded on Jan. 8, 2019 from http://www.rousselet-robatel.com/applications/cannabis-refining/.
Delta Separations; Delta Separations CUP; Retrieval date Nov. 29, 2018; Downloaded from https://www.youtube.com/watch?v=PfgFh6ksBKs&feature=youtu.be; Prior art at least as of Jun. 19, 2017.
Medium; Cannabis Tech Hardware Wunderkind; Retrieval date Nov. 29, 2018; Downloaded from https://medium.com/@Pustejovsky/cannabis-tech-hardware-wunderkind-56946f744d1c; Prior art at least as of Nov. 8, 2017.
Alibaba; Hisen Top Sales CBD Distillate Isolation Agitated Nutsche Filter; Downloaded Feb. 21, 2020; Available from Internet <URL: https://yuanhuai.en.alibaba.com/product/62409002646-812229839/Hisen_Top_Sales_CBD_Distillate_Isolation_Agitated_Nutsche_Filter.html>.

* cited by examiner

CANNABIDIOL ISOLATE PRODUCTION SYSTEMS AND METHODS

BACKGROUND

Field

Various embodiments disclosed herein relate to systems and methods for the production of cannabidiol (CBD) isolate.

DESCRIPTION OF RELATED ART

The production of isolated materials through a crystallization process is a common practice in various fields, particularly in the chemical arts and the pharmaceutical industry. Crystallization is the solidification of atoms or molecules into a highly structured form called a crystal. Usually, this refers to the slow precipitation of crystals from a solution of a substance. However, crystals can form from a pure melt or directly from deposition from the gas phase. Crystallization can also refer to the solid-liquid separation and purification technique in which mass transfer occurs from the liquid solution to a pure solid crystalline phase.

Although crystallization may occur during precipitation, the two terms are not interchangeable. Precipitation simply refers to the formation of an insoluble (solid) from a chemical reaction. A precipitate may be amorphous or crystalline. Other common elements of a crystallization process include at least one temperature change and some form of agitation to assist in the progress of the crystallization process. Different crystallization techniques use a variety of starting materials, including different types of solvents, and varied machinery depending on the type of crystallization taking place.

The production of CBD isolate from CBD oil and a solvent is a relatively new process. Different methods of CBD isolate production use assorted types of complex machinery, including various combinations of reactor tanks, filter dryers, centrifuges, and dryers to collect CBD in a relatively pure form. CBD is a popular compound due to its multitude of health benefits, including pain relief, appetite stimulation, and muscle spasm suppression, among others. Due to the ever increasing demand for CBD and CBD-related products, there is a growing need for efficient and effective ways to produce CBD isolate from CBD oil.

SUMMARY

This disclosure includes methods for CBD isolate production. Some embodiments include a method of producing CBD isolate comprising dissolving, via an agitated vessel, CBD oil in a solvent to thereby form a slurry comprising CBD isolate and excess solvent, sending at least a portion of the slurry from the agitated vessel to an agitated Nutsche filter dryer, and pressurizing an internal portion of the agitated Nutsche filter dryer to remove the excess solvent and capture the CBD isolate in a filter of the agitated Nutsche filter dryer. In some embodiments, the pressurizing comprises applying a vacuum to the internal portion of the agitated Nutsche filter dryer to remove the excess solvent and capture the CBD isolate in the filter of the agitated Nutsche filter dryer. The method may further comprise drying, via the agitated Nutsche filter dryer, at least a portion of the CBD isolate. Some embodiments comprise drying at least a majority of the CBD isolate. In some embodiments, the solvent comprises at least one of pentane and heptane. In some embodiments, the solvent comprises any other suitable solvent.

In some embodiments, the method further comprises applying a vacuum to the internal portion of the agitated Nutsche filter dryer, wherein the drying occurs in response to applying the vacuum. The method may further comprise heating the internal portion of the agitated Nutsche filter dryer, wherein the drying occurs further in response to the heating. The method may further comprise, prior to the drying, washing the CBD isolate with a wash solvent. In some embodiments, the wash solvent defines a temperature that is less than or equal to −10 degrees C. In some embodiments, the wash solvent may be different from the solvent. The method may further comprise collecting excess wash solvent.

In some embodiments, prior to the sending, the method comprises agitating the slurry via the agitated vessel. The method may further comprise heating, via a jacket of the agitated vessel, the slurry to reach a dissolving temperature whereby the CBD oil dissolves in the solvent. In some embodiments, the method further comprises cooling, via a jacket of the agitated vessel, the slurry to reach a crystallization temperature whereby CBD crystals precipitate. The method may further comprise precipitating the CBD isolate in response to the cooling. Additionally, the method may further comprise collecting the CBD isolate in a collection vessel of the agitated Nutsche filter dryer. In some embodiments, the method further comprises pressurizing the internal portion of the agitated Nutsche filter dryer to a gauge pressure of up to 10 barg.

In some embodiments, the method includes dissolving, via an agitated Nutsche filter dryer, CBD oil in a solvent to thereby form a slurry comprising CBD isolate and excess solvent and pressurizing an internal portion of the agitated Nutsche filter dryer to remove the excess solvent and capture the CBD isolate in a filter of the agitated Nutsche filter dryer. In some embodiments, the pressurizing comprises applying a vacuum to the internal portion of the agitated Nutsche filter dryer to remove the excess solvent and capture the CBD isolate in a filter of the agitated Nutsche filter dryer. The method may further comprise drying, via the agitated Nutsche filter dryer, at least a portion of the CBD isolate. In some embodiments, the method further comprises prior to the drying, washing the CBD isolate with a wash solvent.

In some embodiments, the agitated Nutsche filter dryer is jacketed. Accordingly, the method may further comprise heating, via a jacket of the agitated Nutsche filter dryer, the slurry to reach a dissolving temperature whereby the CBD oil dissolves in the solvent. The method may further comprise cooling, via a jacket of the agitated Nutsche filter dryer, the slurry to reach a crystallization temperature whereby CBD crystals precipitate.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments. Various components in the drawings may not be drawn to scale.

DETAILED DESCRIPTION

Figure 1:
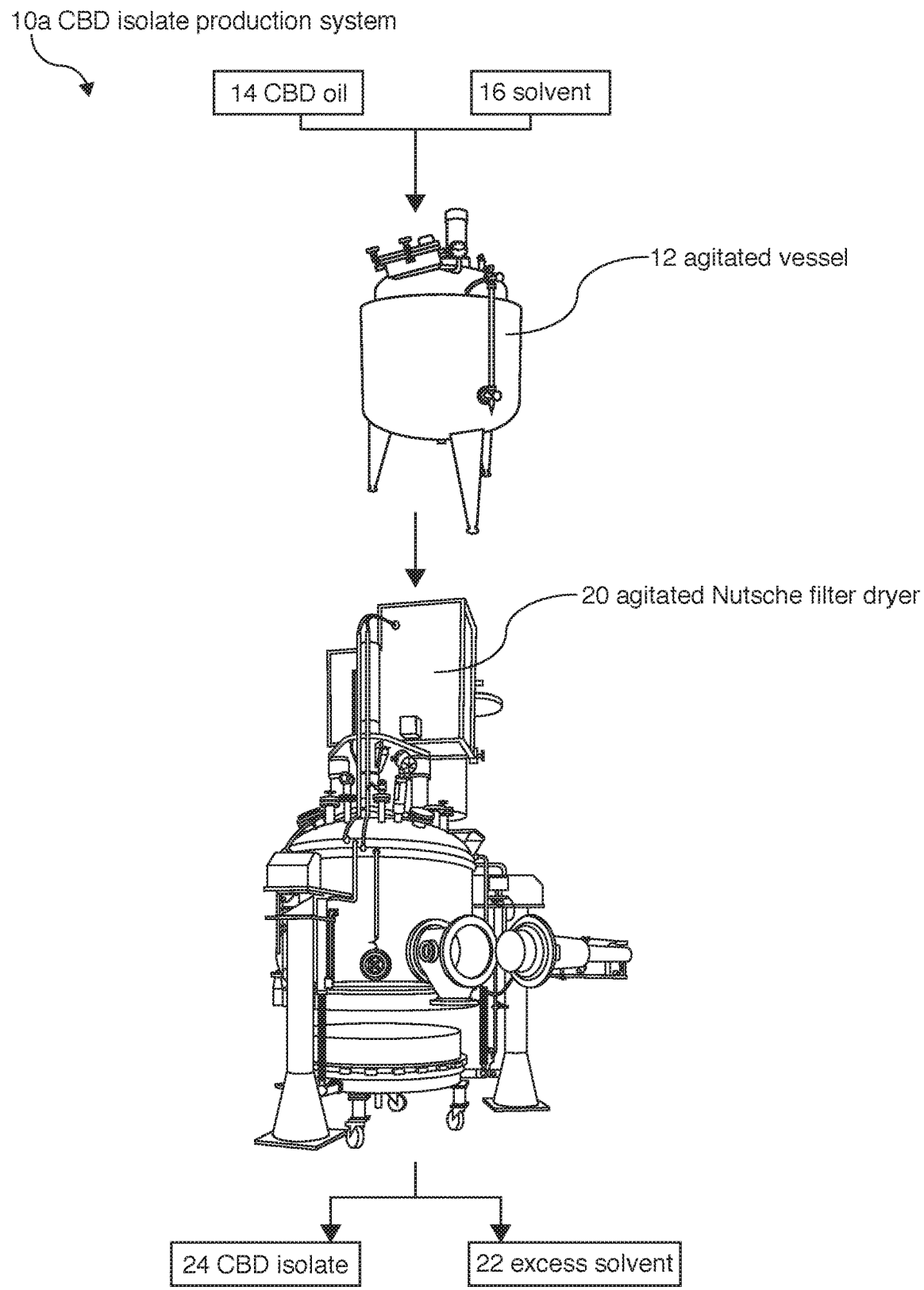
FIG. 1 illustrates a schematic view of a CBD isolate production system, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any system or method disclosed herein, the acts or operations of the system or method may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, methods, and/or procedures described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

INDEX OF COMPONENTS

10a—CBD isolate production system
10b—CBD isolate production system
12—agitated vessel
14—CBD oil
16—solvent
18—slurry
18a—at least a portion of the slurry
20—agitated Nutsche filter dryer
22—excess solvent
24—CBD isolate
24a—at least a portion of the CBD isolate
26—wash solvent
28—excess wash solvent
30—collection vessel
Introduction Crystallization is the solidification of atoms or molecules into a highly structured form called a crystal. Usually, this refers to the slow precipitation of crystals from a solution of a substance. Agitation, centrifugation, and/or temperature change may be used to assist the process in precipitating the desired compound. The solvent and the solid crystals may be separated using a variety of methods, including vacuum filtration, and the solid crystals may undergo further manipulation, such as drying, prior to collection. In some cases, the solvent may be collected for use in a subsequent crystallization processes.

In an example of CBD isolate crystallization process, the process begins with the combination of CBD oil and a solvent, such as pentane, heptane, or other suitable solvent. In some embodiments the CBD oil may be extracted from hemp and/or *cannabis* material by the process described in U.S. patent application Ser. No. 16/286,134 ("the '134 application"); filed on Feb. 26, 2019; and titled "Biomass Extraction and Centrifugation Systems and Methods", which is hereby incorporated by reference.

Following extraction and collection of CBD oil and prior to the crystallization process, the oil may undergo winterization. The winterization process uses freezing and separation to remove waxes and fats from the cannabinoids, thus resulting in an extract of greater purity. The frozen waxes and fats may be separated from the rest of the extract through a manual or an automated process. Following winterization, the CBD oil is ready to be used in the crystallization of CBD isolate crystals.

Referring now to the Figures, FIG. 1 illustrates a schematic view and gives a general idea of the path of materials as they move through the CBD isolate production process of a CBD isolate production system 10a. In some embodiments, the system 10a comprises an agitated vessel 12 and an agitated Nutsche filter dryer 20. In many embodiments, the agitated vessel 12 and the agitated Nutsche filter dryer 20 are fluidly coupled. The agitated vessel 12 may receive CBD oil 14 and a solvent 16, and the agitated Nutsche filter dryer 20 may separate and dry CBD isolate crystals 24 from excess solvent 22. The fluid coupling of the components in the system 10a may create a closed system capable of continuously receiving CBD oil 14 and solvent 16 and processing the ingredients to yield CBD isolate 24 and excess solvent 22. The solvent 16 may be at least one of pentane, heptane, and/or any other suitable solvent. It should be noted that though an agitated Nutsche filter dryer is specifically discussed throughout this disclosure, other types of filter dryers may be utilized to perform the methods described herein. In some embodiments, a Comber Nutsche filter dryer (sold by Comber Process Technology S.r.l. having an office in Agrate Brianza, Monza e Brianza, Italy) is used. Methods of producing the CBD isolate 24 and excess solvent 22 from the CBD oil 14 and solvent 16 will be discussed in detail with reference to FIGS. 2A-4F.

Figure 2A:
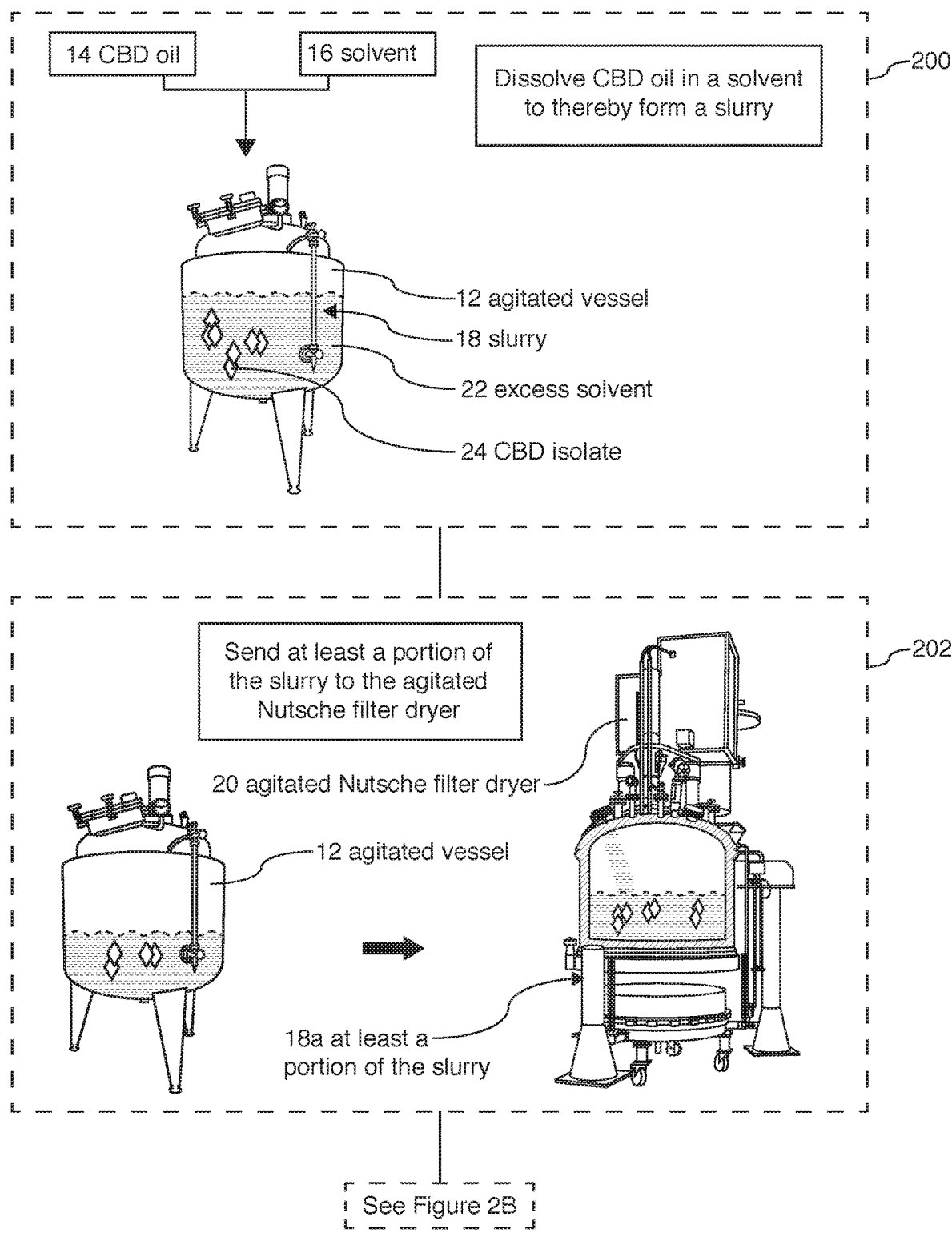
FIGS. 2A and 2B illustrate a method of producing CBD isolate, according to some embodiments.
Figure 2B:
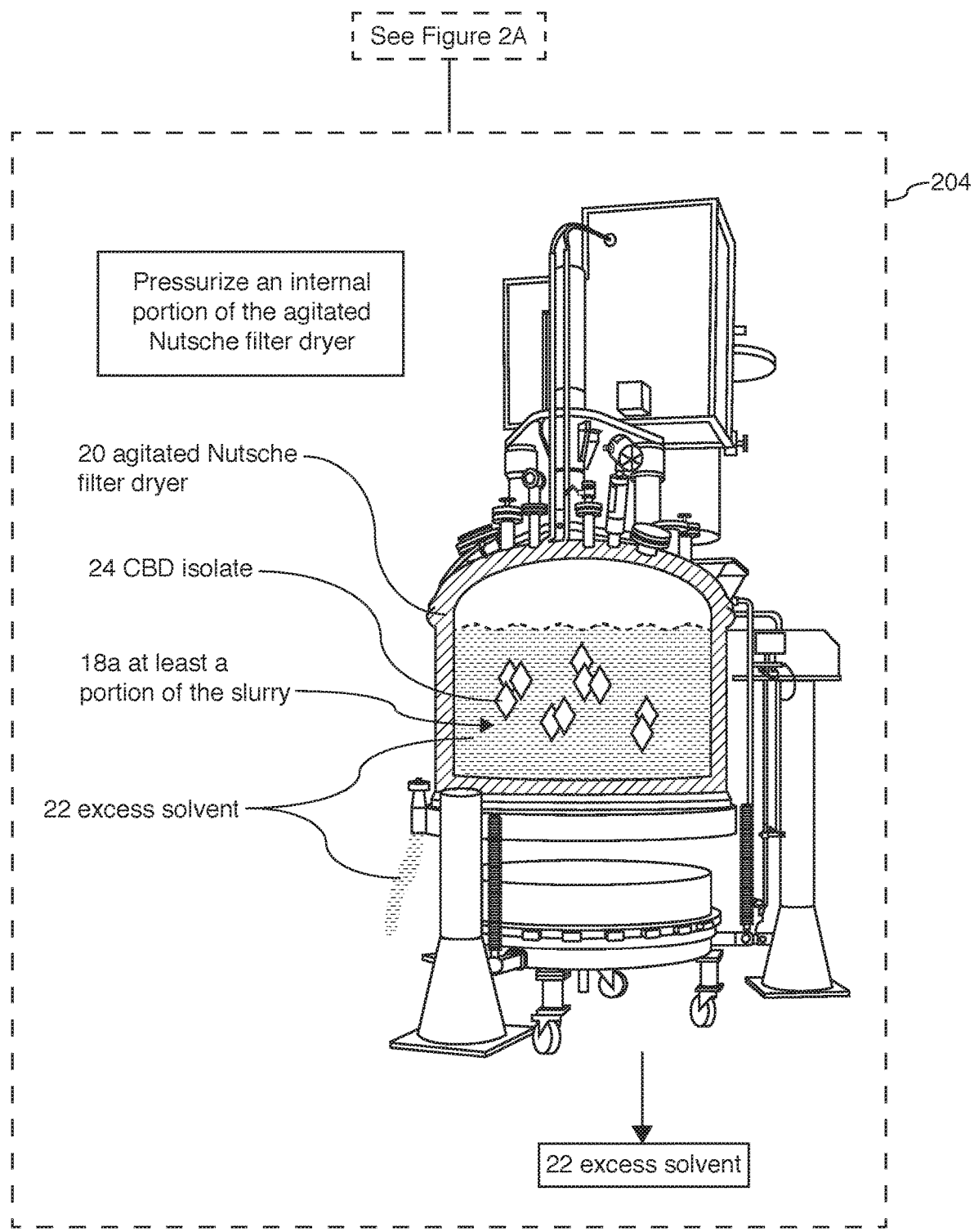

FIGS. 2A and 2B illustrate a method of producing CBD isolate, according to some embodiments. As shown in FIG. 2A at step 200, the method may comprise dissolving, via an agitated vessel 12, CBD oil 14 in a solvent 16 to thereby form a slurry 18 comprising CBD isolate 24 and excess solvent 22. For purposes of this disclosure, the terms "slurry" and "solution" may be used interchangeably. However, the respective terms may be used to represent specific situations whereby a "solution" is formed upon dissolving of CBD oil 14 in the solvent 16, and whereby a "slurry" is then formed once CBD isolate crystals 24 precipitate out of the "solution."

In some embodiments, discharging the CBD oil 14 and the solvent 16 into the agitated vessel 12 takes between about 15 and 30 minutes. The discharging make take more or less time, depending on the quantity of the CBD oil 14 and the solvent 16 being discharged into the agitated vessel 12.

The slurry 18 may comprise a specific ratio of CBD oil 14 to solvent 16. The amount and ratio of CBD oil 14 to solvent 16 input into the system 10a may depend on the type, as well as the particular physical and chemical properties of both the CBD oil 14 and the solvent 16 used in the system 10*a*. In several embodiments, the ratio of the CBD oil 14 to the solvent 16 is substantially constant to ensure a repeatable process, as well as a consistent and repeatable crystallization result.

According to step 202, the method may further comprise sending at least a portion of the slurry 18*a* from the agitated vessel 12 to an agitated Nutsche filter dryer 20. The sending step 202 may take about 15 to 30 minutes, depending on the quantity of the slurry 18. In some embodiments, at least a portion of the slurry 18*a* is sent to the agitated Nutsche filter dryer 20 via a fluid coupling mechanism comprising at least one tube, pipe, or the like. The fluid coupling mechanism may be coupled to at least one pump to facilitate the sending. In some embodiments, the agitated vessel 12 is elevated and the system 10*a* uses gravity to transfer the at least a portion of the slurry 18*a* through the fluid coupling mechanism to the agitated Nutsche filter dryer 20.

FIG. 2B at step 204 shows that, in some embodiments, the method further comprises pressurizing an internal portion of the agitated Nutsche filter dryer 20 to remove the excess solvent 22 and capture the CBD isolate 24 in a filter of the agitated Nutsche filter dryer 20. The pressurizing may comprise applying a vacuum to the internal portion of the agitated Nutsche filter dryer 20. In some embodiments, the vacuum is achieved by applying a vacuum directly via the agitated Nutsche filter dryer 20. In some embodiments, the vacuum is applied using an external component coupled to the agitated Nutsche filter dryer 20. In some embodiments, the vacuum functions to pull the excess solvent 22 through the filter of the agitated Nutsche filter dryer 20 while collecting the CBD isolate crystals 24 against the filter. The excess solvent 22 may be collected for use in a subsequent round of producing CBD isolate. In some embodiments, the pressurizing results in the pressure of the internal portion of the agitated Nutsche filter dryer 20 reaching a gauge pressure up to about 10 barg. The pressurizing step 204 may take between about 15 and 30 minutes, depending on the quantity of the at least a portion of the slurry 18*a*. The pressurizing step could take more or less time depending on the characteristics of the CBD isolate crystals 24.

Figure 3A:
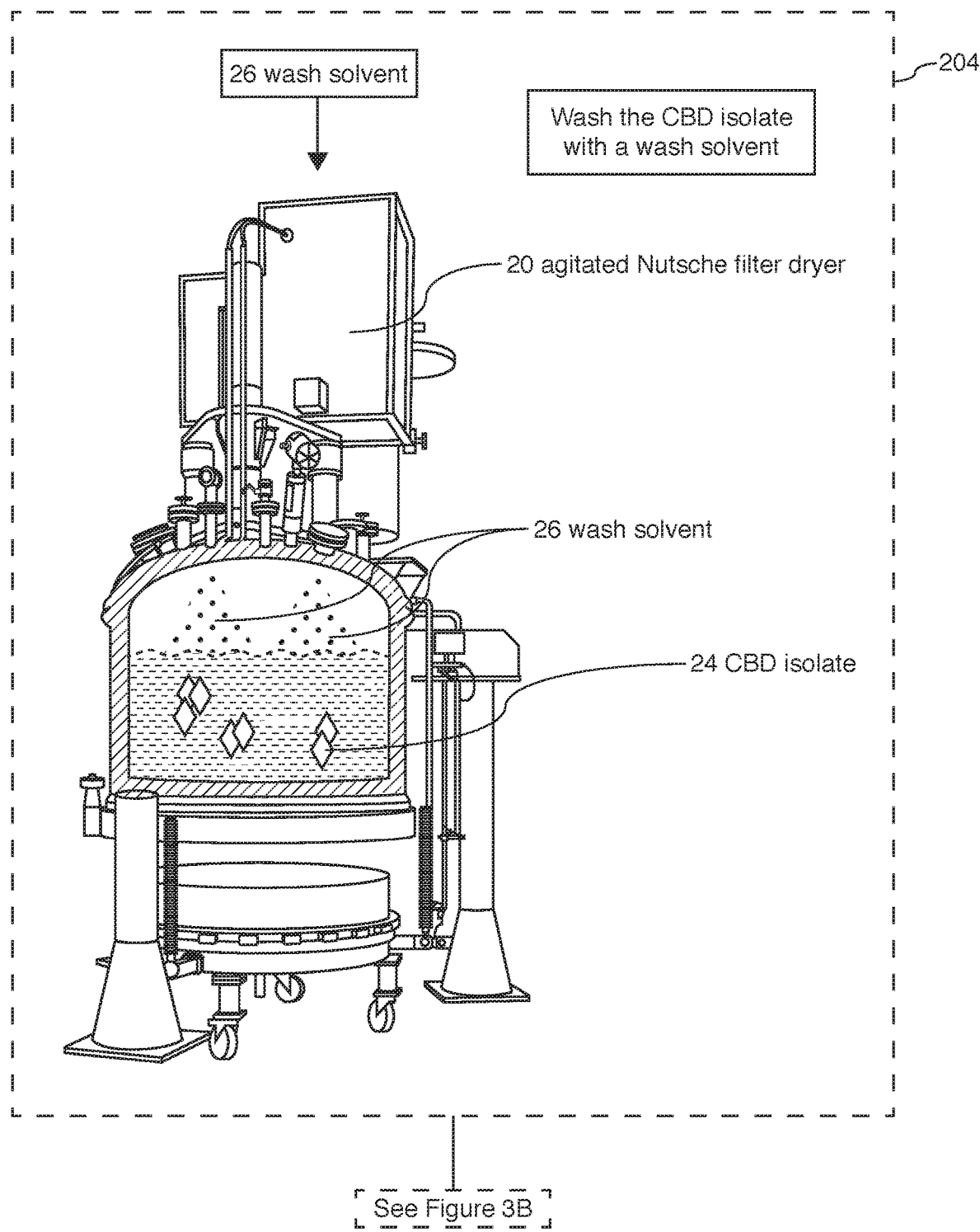
FIGS. 3A and 3B illustrate a method of producing CBD isolate, according to some embodiments.
Figure 3B:
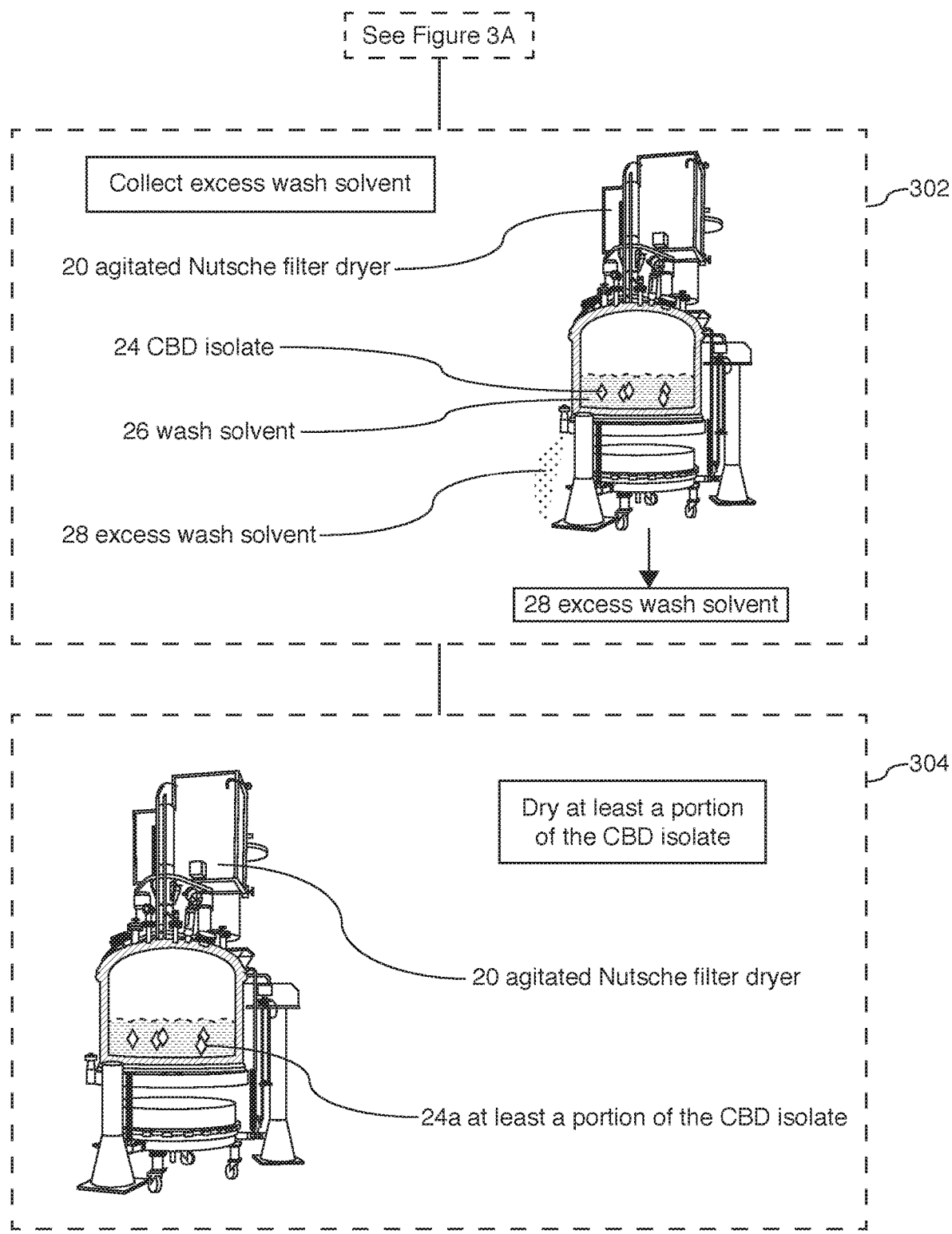

FIGS. 3A and 3B introduce additional steps, beginning with step 300, which may be performed after step 204. Step 300 includes washing the CBD isolate 24 with a wash solvent 26. In many embodiments, the wash solvent 26 is a cold solvent at a temperature less than or equal to about −10 degrees C. In some embodiments, the wash solvent 26 is different than the solvent 16 used to dissolve the CBD oil 14 and form the slurry 18. Prior to the washing, the wash solvent 26 may be held in a separate component of the system 10*a* and added in a manner similar to the sending step described with reference to FIG. 2A at step 202; i.e. through a fluid coupling mechanism. In some embodiments, the washing step 300 facilitates further purification of the CBD isolate 24 by removing residual excess solvent 22 and any other impurities that remain in the at least a portion of the slurry 18*a* after the pressurizing step 204.

As illustrated in FIG. 3B, step 302 comprises collecting excess wash solvent 28. Similar to the excess solvent 22 collected in step 204, the excess wash solvent 28 may be collected for use in a subsequent round of producing CBD isolate. In some embodiments, collecting the excess wash solvent 28 comprises collecting substantially the same quantity of wash solvent 26 added to the agitated Nutsche filter dryer 20 in the washing step 300. The method may further comprise drying, via the agitated Nutsche filter dryer 20, at least a portion of the CBD isolate 24*a*, as illustrated by step 304. Similar to the pressurizing step 204, the drying step 304 may comprise applying a vacuum to the internal portion of the agitated Nutsche filter dryer 20. In some embodiments, the drying occurs in response to applying the vacuum, and applying the vacuum allows drying to occur at a lower temperature. The drying may also occur further in response to heating the internal portion of the agitated Nutsche filter dryer 20. Heating the internal portion of the agitated Nutsche filter dryer 20 may be achieved in substantially the same way as the heating step 404, discussed below with reference to FIG. 4B. The drying step 304 may take between about 1 and 2 hours. The drying time could be more or less, depending on the quantity of the at least a portion of the CBD isolate 24*a* as well as the amount of moisture in the portion.

The vacuum drying step 304 may be achieved by applying a vacuum via the agitated Nutsche filter dryer 20. The vacuum may be applied using an external component coupled to the agitated Nutsche filter dryer 20. In some embodiments, applying the vacuum further comprises agitation such that the at least a portion of the CBD isolate 24*a* is agitated (e.g., via an agitator within the agitated Nutsche filter dryer 20) to facilitate release of residual wash solvent 26. The residual wash solvent 26 may be condensed by a condenser of the agitated Nutsche filter dryer 20 and collected for use in a subsequent round of producing CBD isolate. In some embodiments, the pressurizing step 204 and the drying step 304 use the same mechanism(s) and machinery for applying the vacuum. In other embodiments, the pressurizing step 204 and the drying step 304 use different mechanism(s) and machinery for applying the vacuum.

Figure 4A:
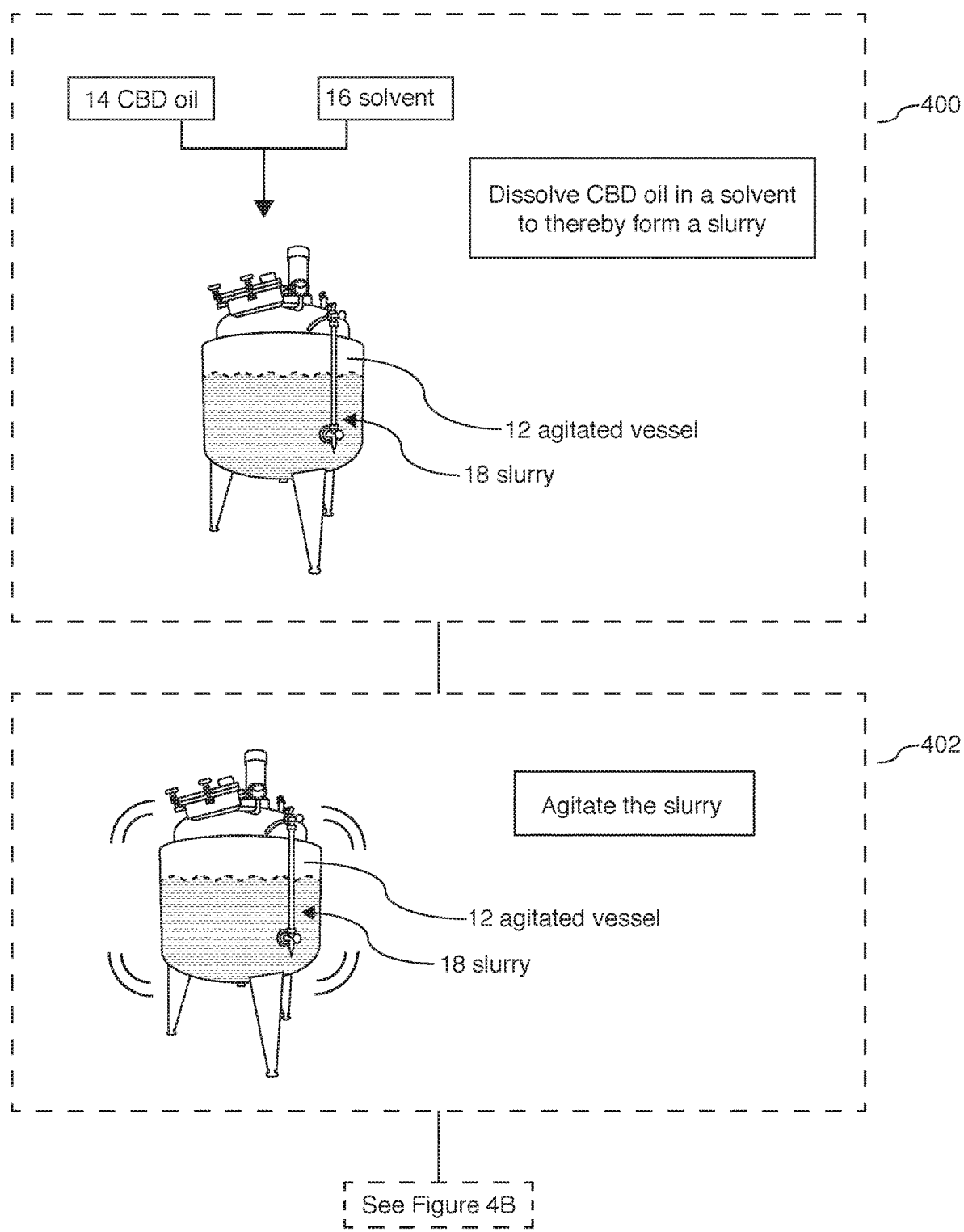
FIGS. 4A, 4B, 4C, 4D, 4E, and 4F illustrate a method of producing CBD isolate, according to some embodiments.

FIGS. 4A, 4B, 4C, 4D, 4E, and 4F show a method of producing CBD isolate, according to some embodiments. The method may begin with step 400: dissolving, via an agitated vessel 12, CBD oil 14 in a solvent 16 to thereby form a slurry 18 comprising CBD isolate 24 and excess solvent 22. In some embodiments, step 400 is substantially the same as step 200 from FIG. 2A, respectively. FIG. 4A introduces an added method step at step 402: agitating the slurry 18 via the agitated vessel 12. As mentioned previously in this disclosure, agitation may be used to facilitate the formation of crystals in a crystallization process. In some embodiments, agitation is not necessary to successfully precipitate CBD isolate 24. Examples of agitation may include stirring and/or mixing the slurry 18 within the agitated vessel 12, and/or any other suitable form of agitation. Some forms of agitation, such as stirring and/or mixing the slurry 18, may be achieved through the use of an agitator within the agitated vessel 12. The agitation may work continuously for constant mixing or may operate intermittently for periods of mixing and rest, as appropriate.

In some embodiments, the agitated vessel 12 includes a jacket. According to FIG. 4B, the jacket may be used to alter the temperature of the vessel 12, and therefore the temperature of the contents within the agitated vessel 12. Different types of jackets may be used in different embodiments. For example, a conventional jacket, a half-pipe coil jacket (internal or external), a dimple jacket, and/or a plate-coil jacket may be used to heat and/or cool a solution within each respective vessel to which the jacket is coupled. The change in temperature may be facilitated by liquid and/or gas heating and/or cooling of the jacket, electric heating and/or cooling of the jacket, and any other appropriate methods. Other appropriate methods of heating and/or cooling may include at least partially immersing a hot or cold coil in the slurry 18 and using an external heat exchanger to facilitate heating and/or cooling of the slurry 18 whereby the solution is circulated between the vessel and heat exchanger where the actual heating and/or cooling takes place.

Step 404 shows heating, via the jacket of the agitated vessel 12, the slurry 18 to reach a dissolving temperature whereby the CBD oil 14 dissolves in the solvent 16. In some embodiments, the dissolving temperature is greater than or equal to about 40 degrees C. The dissolving temperature may vary based on any number of factors in the crystallization process, including the type of solvent 16 used, the amount of CBD oil 14 and solvent 16 used, the presence of impurities in the CBD oil 14, and various other factors. In some embodiments, the heating step 404 takes about 30 minutes to reach the dissolving temperature and ensure that the CBD oil 14 dissolves substantially completely in the solvent 16.

Figure 4B:
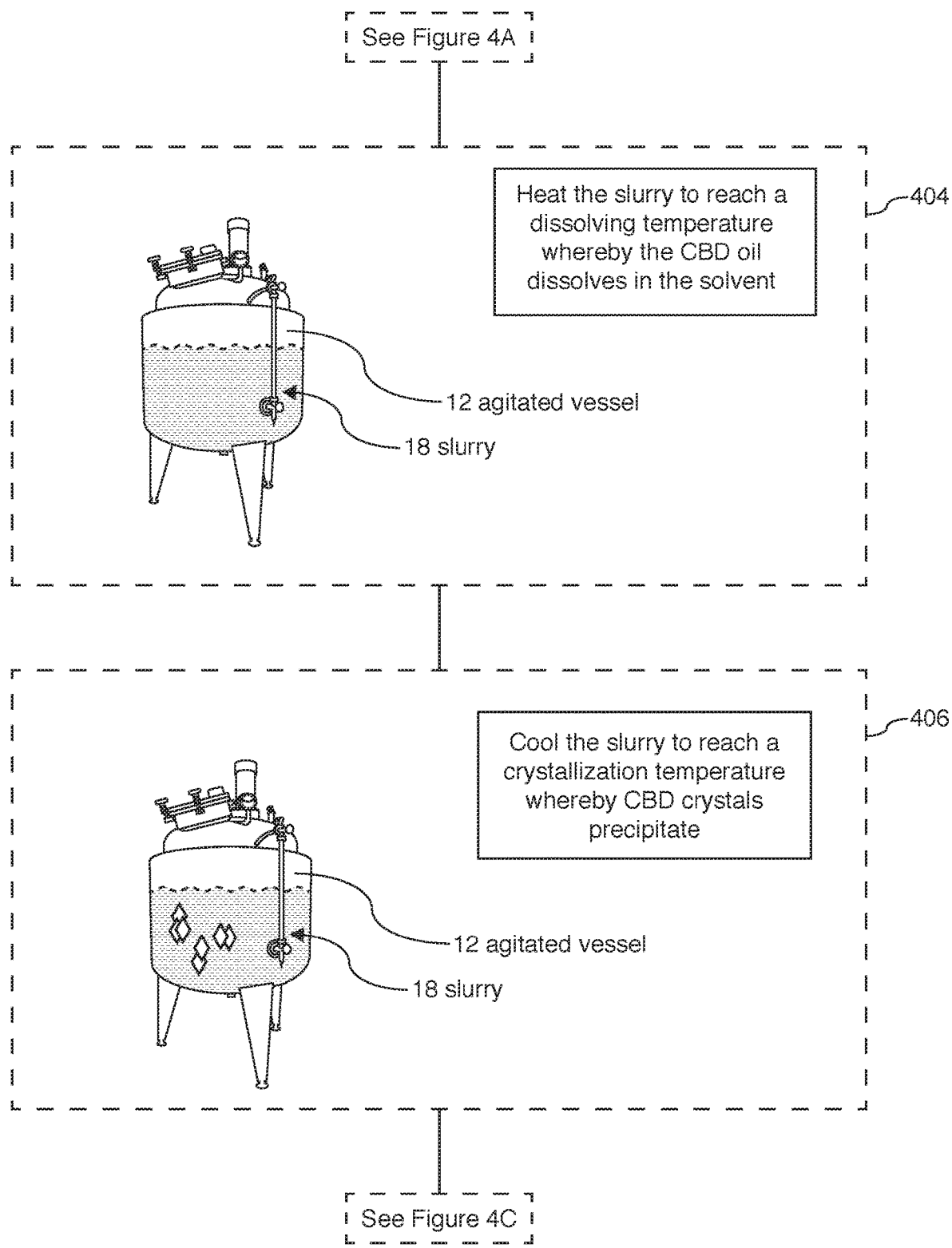

After heating the slurry to dissolve the CBD oil 14, the method may further comprise cooling, via the jacket of the agitated vessel 12, the slurry to reach a crystallization temperature whereby CBD crystals precipitate, as shown in step 406 of FIG. 4B. In some embodiments, the crystallization temperature is less than or equal to about −10 degrees C. The crystallization temperature may vary based on any number of factors in the crystallization process, including the type of solvent 16 used, the amount of CBD oil 14 and solvent 16 used, the presence of impurities in the CBD oil 14, and various other factors. In some embodiments, the cooling step 406 takes between about 30 minutes and 1 hour to reach the crystallization temperature and ensure that the CBD isolate 24 precipitates out of the slurry 18. FIG. 4B at step 406 also shows the presence of CBD isolate 24, represented as crystals, inside the agitated vessel 12 as part of the slurry 18. It should be noted that though a crystal shape throughout the Figures represents the CBD isolate 24, the isolate 24 may take other forms. It should also be noted that FIGS. 4A and 4B show the agitating step 402 occurring before the heating step 404 and cooling step 406. In some embodiments, the agitating step 402 may occur at least partially simultaneously with at least one of the heating step 404 and the cooling step 406.

In some embodiments, dissolving the CBD oil 14 in the solvent 16 is achieved through the use of a pre-warmed solvent 16. Such an embodiment may not require the heating step described in step 404 of FIG. 4B. The solvent 16 may be warmed in a manner similar to the heating step 404, i.e., through the use of a jacketed vessel containing the solvent 16.

Figure 4C:
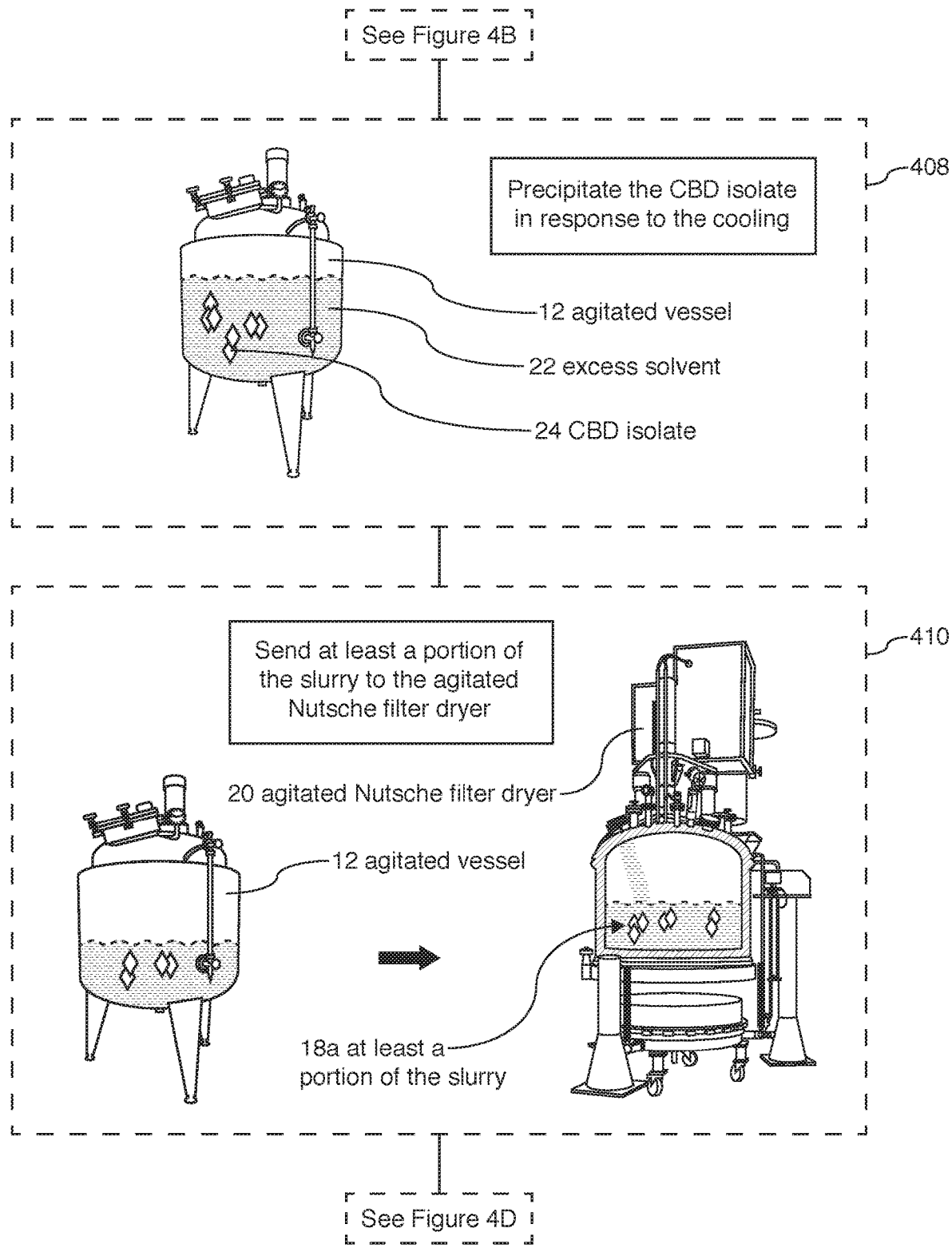
Figure 4D:
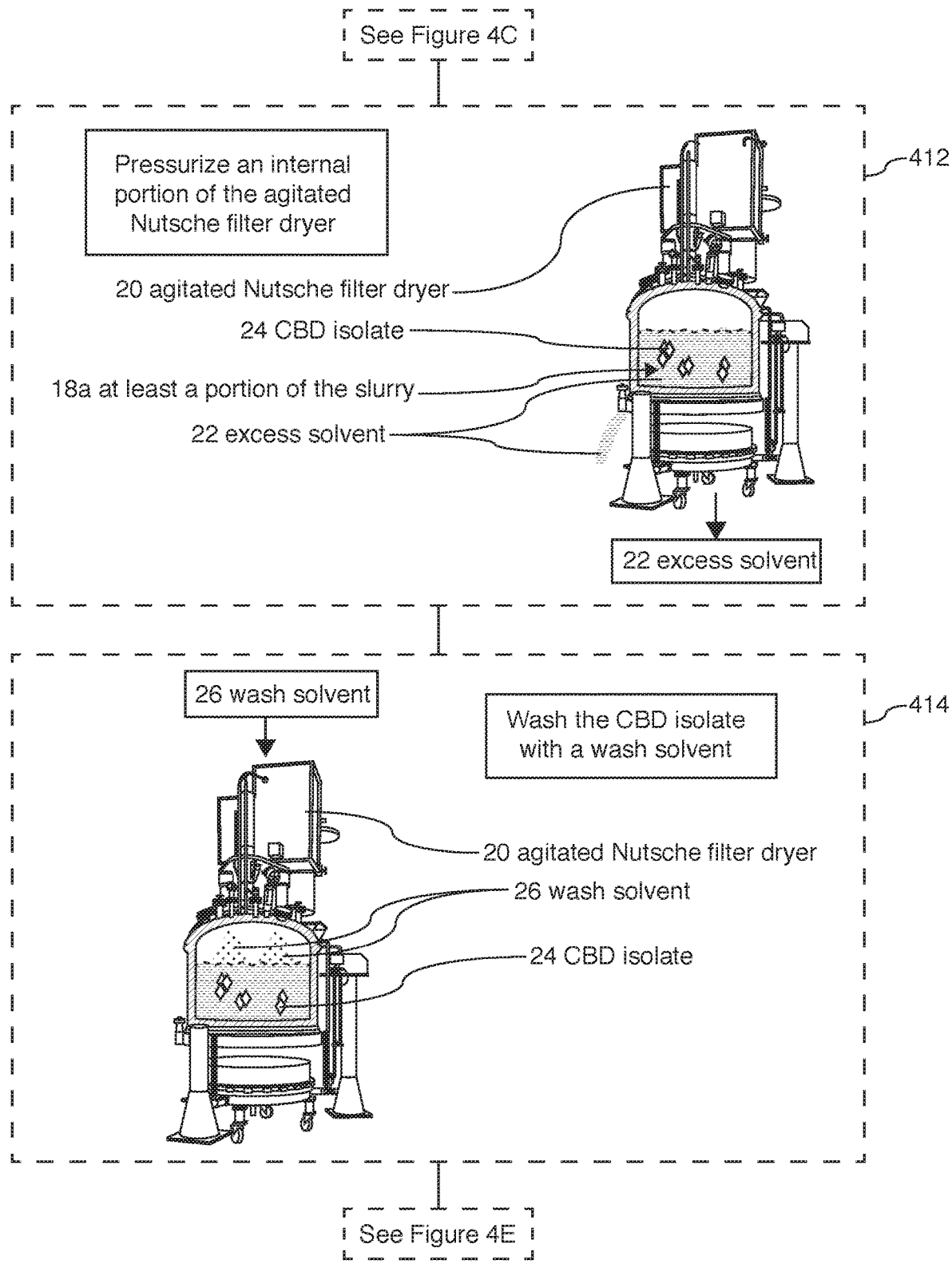

Step 408 in FIG. 4C illustrates precipitating the CBD isolate 24 in response to the cooling. As discussed above, the cooling at step 406 lowers the temperature of the agitated vessel 12 and its contents to about −10 degrees C., which causes the CBD isolate 24 to precipitate out of the slurry 18, and leave behind excess solvent 22. Step 410 illustrates sending at least a portion of the slurry 18a from the agitated vessel 12 to an agitated Nutsche filter dryer 20. FIG. 4D includes steps 412 and 414. Step 412 illustrates pressurizing an internal portion of the agitated Nutsche filter dryer 20 to remove the excess solvent 22 and capture the CBD isolate 24 with a filter of the agitated Nutsche filter dryer 20.

Figure 4E:
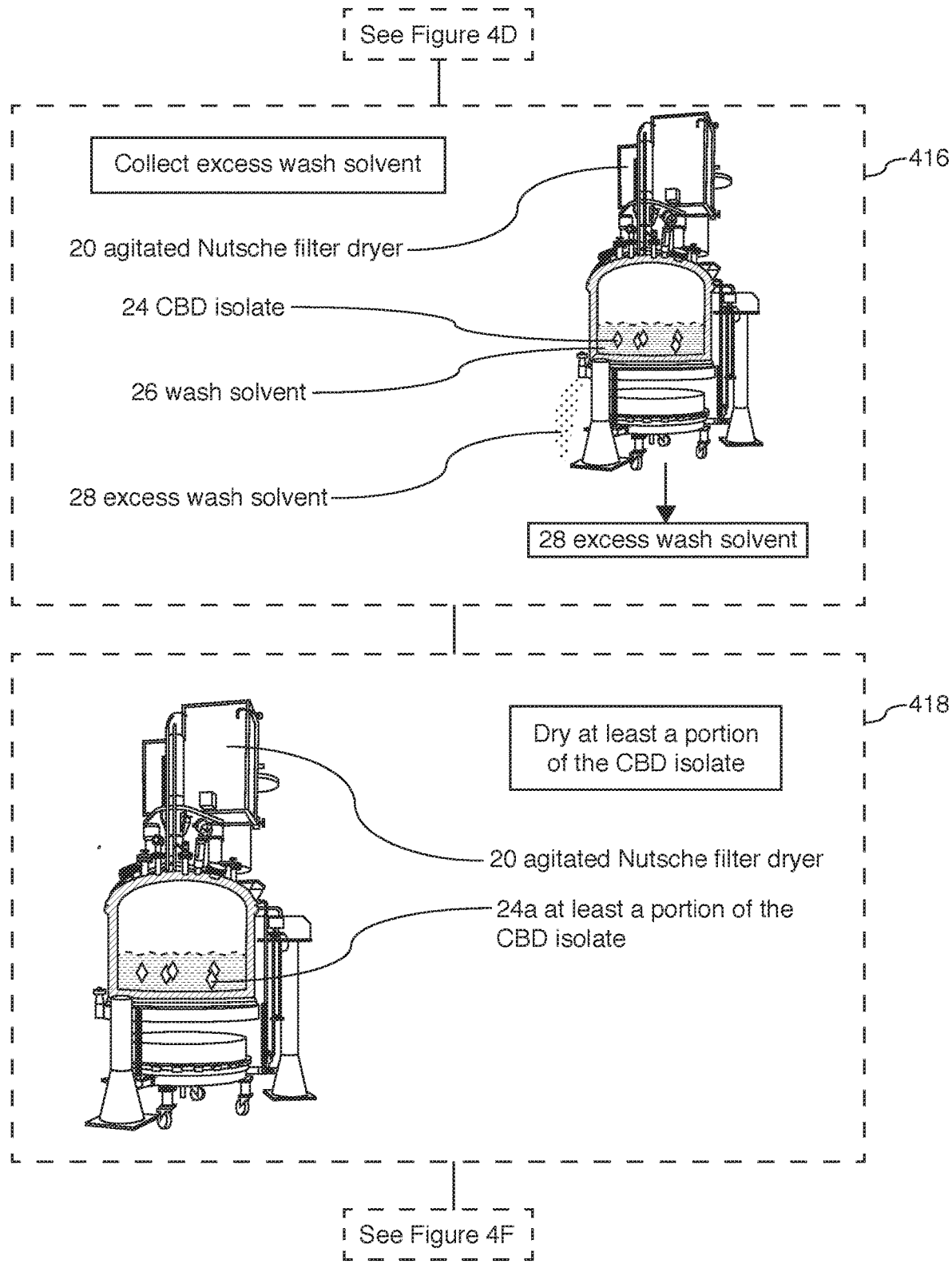
Figure 4F:
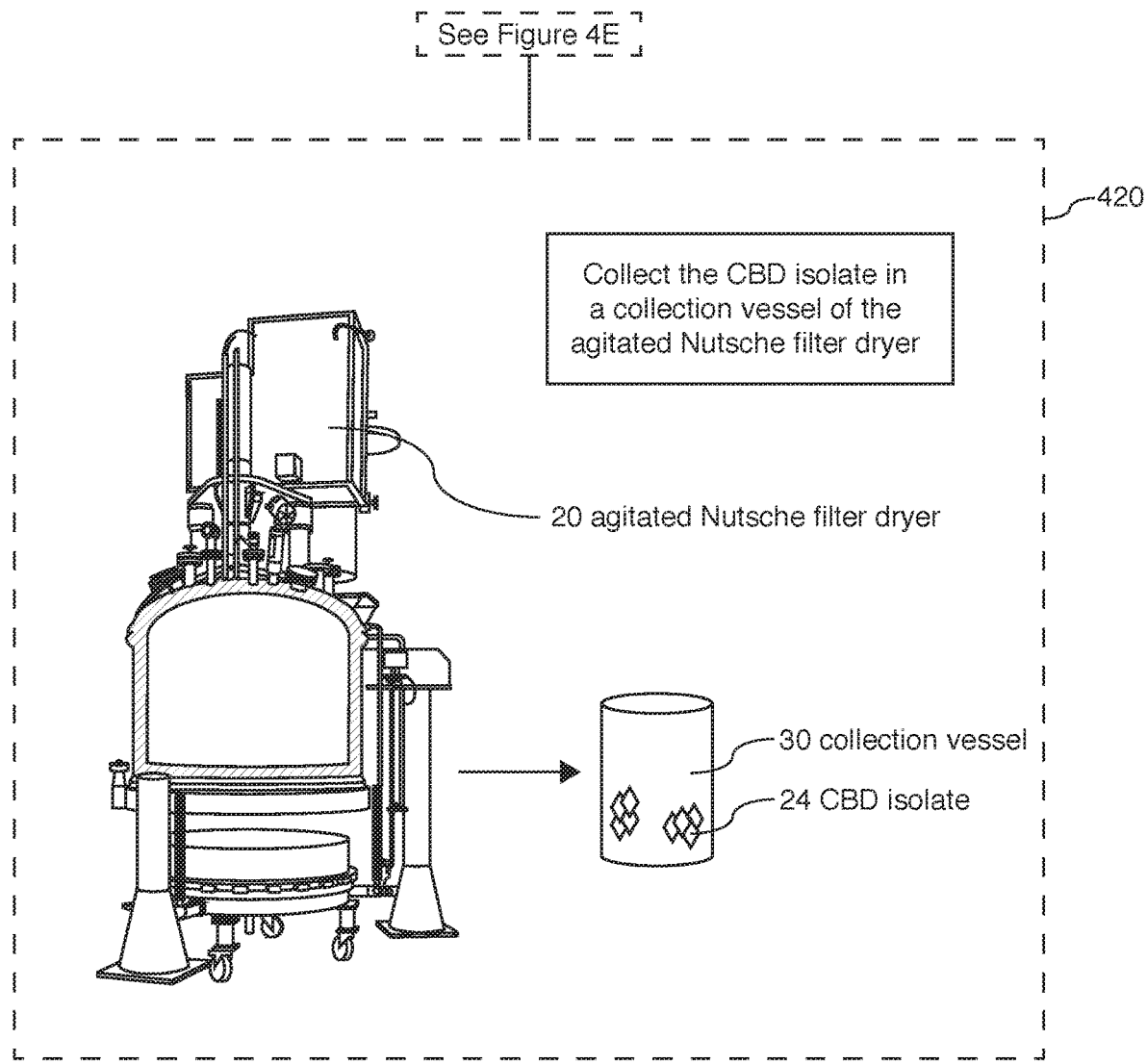

Step 414 shows washing the CBD isolate 24 with a wash solvent 26. Step 416, shown in FIG. 4E, illustrates collecting excess wash solvent 28. Step 418, also shown in FIG. 4E, illustrates drying, via the agitated Nutsche filter dryer 20, at least a portion of the CBD isolate 24a. FIG. 4F includes step 420, which illustrates collecting the CBD isolate 24 in a collection vessel 30 of the agitated Nutsche filter dryer 20. In some embodiments, following collection of the CBD isolate 24, the system 10a may be re-set to start a second (or third, fourth, etc.) round of precipitating CBD isolate 24. The collection vessel 30 may be sized and configured to contain CBD isolate 24 from a single round of crystallization or from multiple rounds. In an embodiment where the collection vessel 30 is configured to contain CBD isolate 24 from multiple rounds of crystallization, the system 10a may run the crystallization process multiple times over a predetermined amount of time and require collection of the isolate 24 from the collection vessel 30 fewer times than the total number of rounds. For example, the crystallization process may occur multiple times during a work shift and the collection vessel 30 may be emptied just once during the shift. Appropriate sizing of the collection vessel 30 may increase efficiency of the system 10a and require reduced human intervention.

Figure 5:
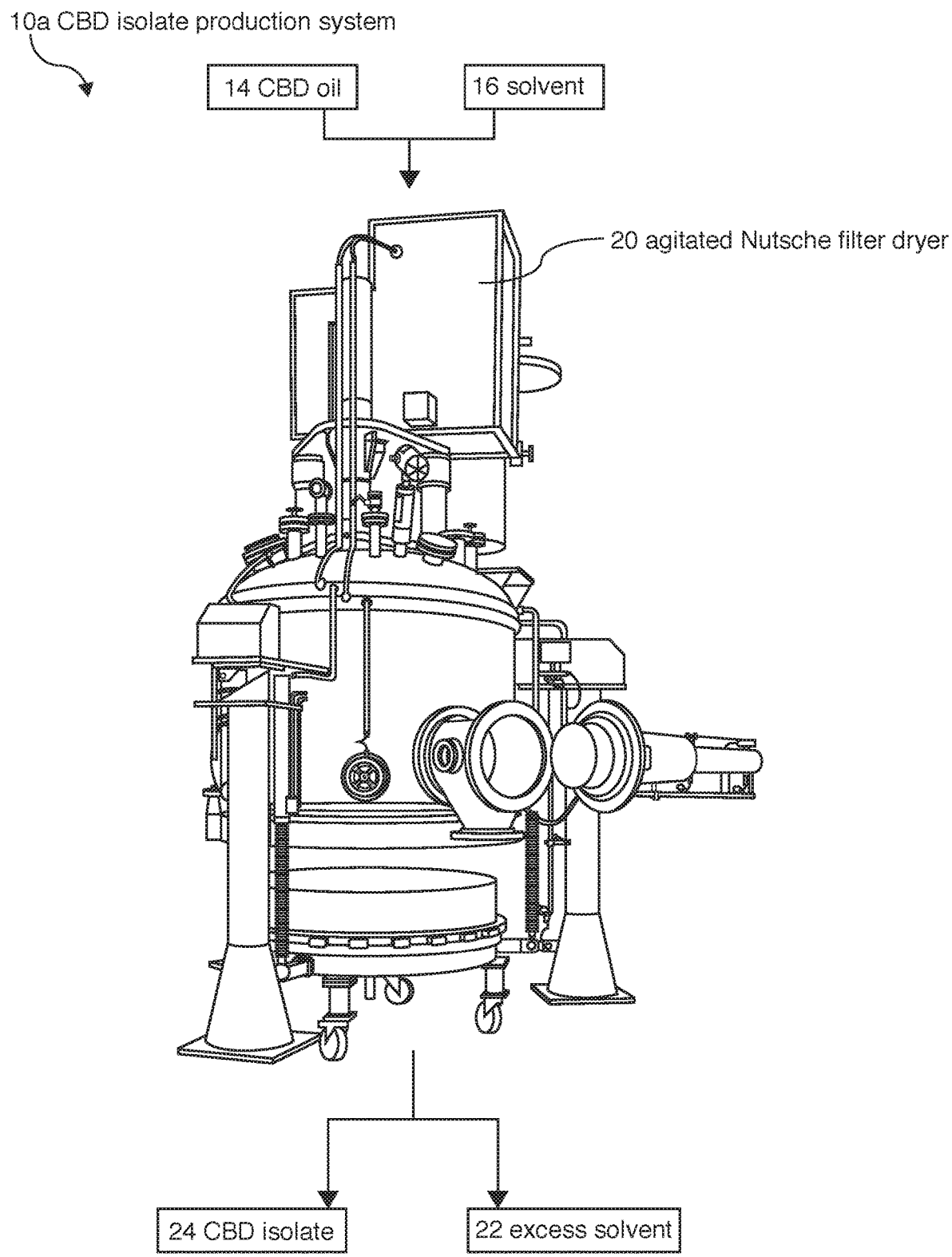
FIG. 5 illustrates a schematic view of a CBD isolate production system, according to some embodiments.

FIG. 5 illustrates a schematic view of a CBD isolate production system 10b. In some embodiments, the system 10b comprises an agitated Nutsche filter dryer 20, which receives CBD oil 14 and a solvent 16, and produces CBD isolate 24 and excess solvent 22. The solvent may be at least one of pentane, heptane, and/or any other suitable solvent. It should be noted that though an agitated Nutsche filter dryer is specifically discussed throughout this disclosure, other types of filter dryers may be utilized to perform the methods described herein. Methods of producing the CBD isolate 24 and excess solvent 22 from the CBD oil 14 and solvent 16 will be discussed in detail with reference to FIGS. 6-8C.

Figure 6A:
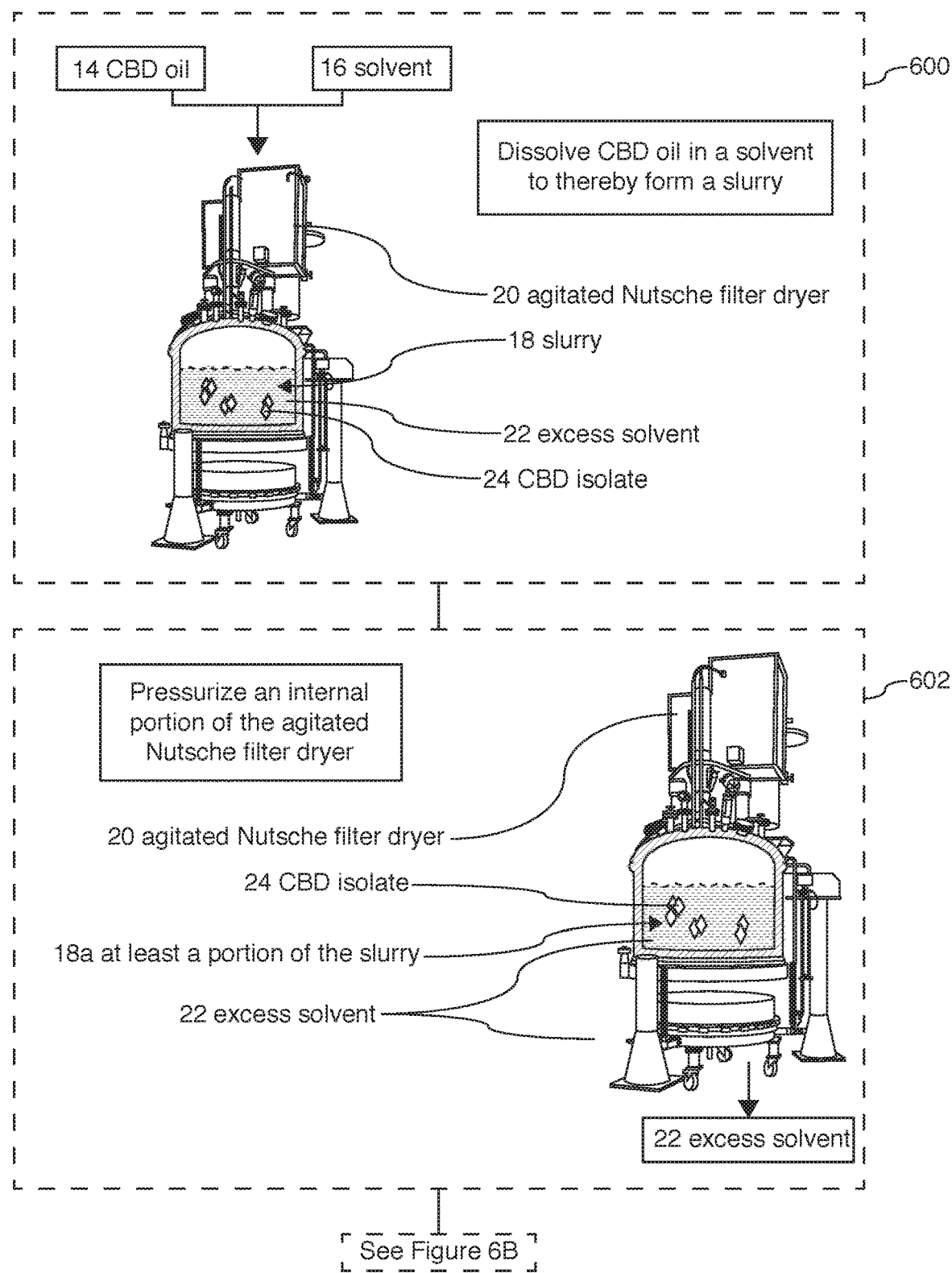
FIGS. 6A and 6B illustrate a method of producing CBD isolate, according to some embodiments.
Figure 6B:
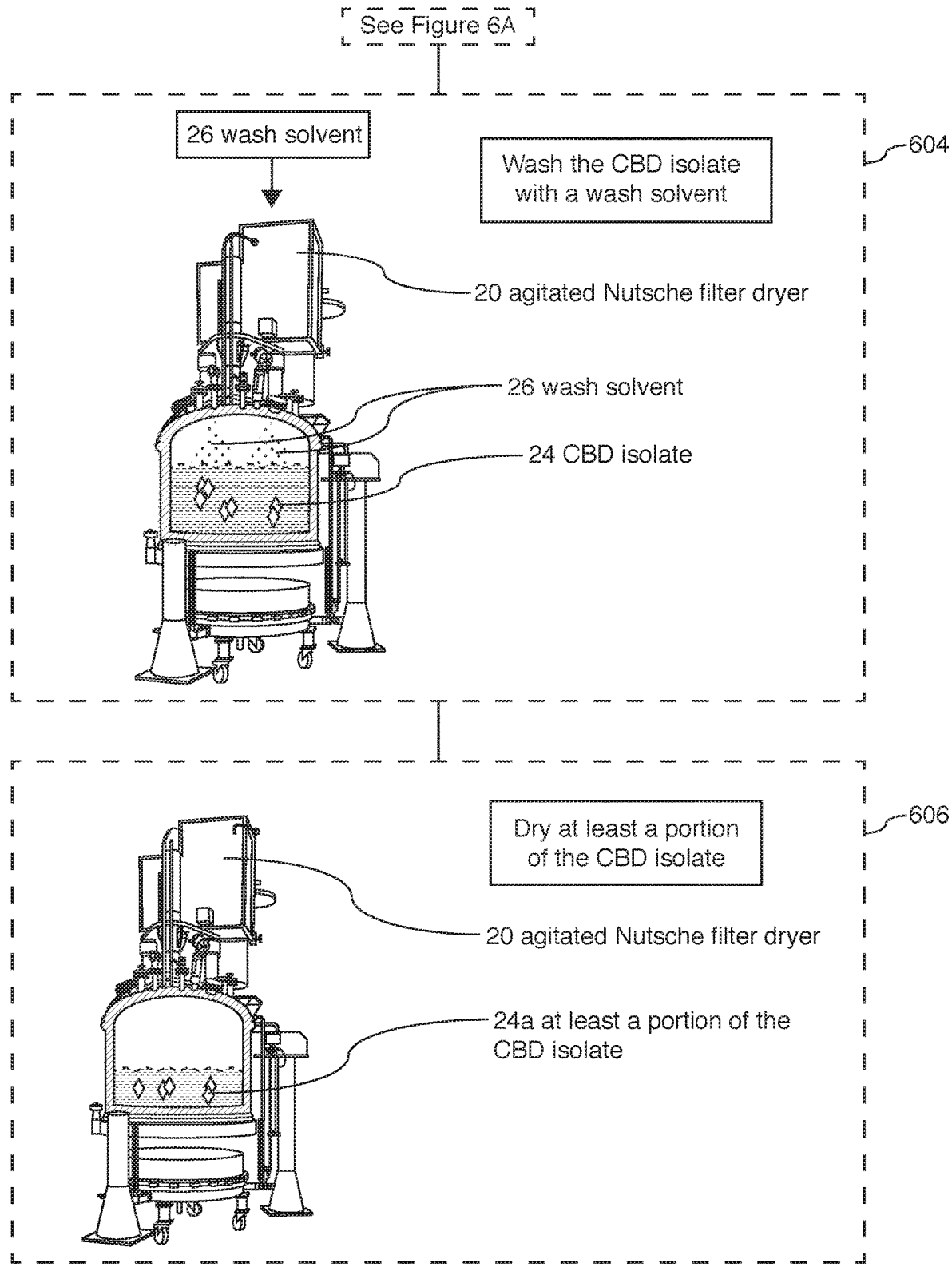

FIGS. 6A and 6B illustrate a method of producing CBD isolate, according to some embodiments. The method may begin with step 600 by dissolving, via an agitated Nutsche filter dryer 20, CBD oil 14 in a solvent 16 to thereby form a slurry 18 comprising CBD isolate 24 and excess solvent 22. Step 600 demonstrates that, in some embodiments, the dissolving step takes place in the agitated Nutsche filter dryer 20 rather than the agitated vessel 12 included in the system 10a. In some embodiments, discharging the CBD oil 14 and the solvent 16 into the agitated Nutsche filter dryer 20 takes between about 15 and 30 minutes. The discharging may take more or less time, depending on the quantity of the CBD oil 14 and the solvent 16 being discharged into the agitated Nutsche filter dryer 20.

The slurry 18 may comprise a specific ratio of CBD oil 14 to solvent 16. The amount and ratio of CBD oil 14 to solvent 16 input into the system 10b may depend on the type, as well as the particular physical and chemical properties of both the CBD oil 14 and the solvent 16 used in the system 10b. In several embodiments, the ratio of the CBD oil 14 to the solvent 16 is substantially constant to ensure a repeatable process, as well as a consistent and repeatable crystallization result.

The method may further comprise pressurizing an internal portion of the agitated Nutsche filter dryer 20 to remove the excess solvent 22 and capture the CBD isolate 24 with a filter of the agitated Nutsche filter dryer 20, shown at step 602. In some embodiments, the pressurizing comprises applying a vacuum to the internal portion of the agitated Nutsche filter dryer 20. The pressurizing may result in the pressure of the internal portion of the agitated Nutsche filter dryer 20 reaching a gauge pressure up to about 10 barg. It should be appreciated that the internal portion of the agitated Nutsche filter dryer 20 may be pressurized to any suitable gauge pressure. The pressurizing step 602 may take between about 15 and 30 minutes, depending on the quantity of the slurry 18. In some embodiments, the vacuum is achieved by applying a vacuum via the agitated Nutsche filter dryer 20. The vacuum may be applied using an external component coupled to the agitated Nutsche filter dryer 20. In some embodiments, the vacuum functions to pull the excess solvent 22 through the filter of the agitated Nutsche filter dryer 20 while collecting the CBD isolate 24 against the filter. The excess solvent 22 may be collected for use in a subsequent round of producing CBD isolate. The pressurizing step could take more or less time depending on the characteristics of the CBD isolate crystals 24.

FIG. 6B demonstrates that, in some embodiments, the method further comprises washing the CBD isolate 24 with a wash solvent 26, as shown in step 604. Similar to the washing steps 306 and 414 discussed with reference to the system 10a, the wash solvent 26 may comprise a cold solvent defining a temperature less than or equal to about −10 degrees C. In some embodiments, the wash solvent 26 is different than the solvent 16 used to dissolve the CBD oil 14 and form the slurry 18. FIG. 6B also includes step 606, which illustrates drying, via the agitated Nutsche filter dryer 20, at least a portion of the CBD isolate 24a. Similar to the drying steps 310 and 418 discussed with reference to the system 10a, the drying may occur in response to a vacuum applied to an internal portion of the agitated Nutsche filter dryer 20. Also similar to the drying steps 310 and 418, the drying may also occur further in response to heating the internal portion of the agitated Nutsche filter dryer 20. The drying step 606 may take between about 1 and 2 hours, depending on the quantity of the at least a portion of the CBD isolate 24a as well as the amount of moisture in the portion.

The applied vacuum of the drying step 606 may be achieved by applying a vacuum directly via the agitated Nutsche filter dryer 20 (i.e., the Nutsche filter dryer 20 may be configured to produce vacuum). However, The vacuum may be applied using an external component coupled to the agitated Nutsche filter dryer 20. In some embodiments, the vacuum further comprises agitation (e.g., via an agitator within the agitated Nutsche filter dryer 20) such that the at least a portion of the CBD isolate 24a is agitated to facilitate release of residual wash solvent 26. The agitation may work continuously for constant mixing or may operate intermittently for periods of mixing and rest, as appropriate.

The residual wash solvent 26 may be condensed by a condenser of the agitated Nutsche filter dryer 20 and collected for use in a subsequent round of producing CBD isolate. In some embodiments, the pressurizing step 602 and the drying step 606 use the same mechanism(s) and machinery for applying the vacuum. In other embodiments, the pressurizing step 602 and the drying step 606 use different mechanism(s) and machinery for applying the vacuum.

Though not shown, in some embodiments the drying step 606 is preceded by collection of excess wash solvent 28, which may be re-used for a subsequent round of CBD isolate crystallization. The drying step 606 may be followed by collection of the CBD isolate 24 (not shown).

Figure 7A:
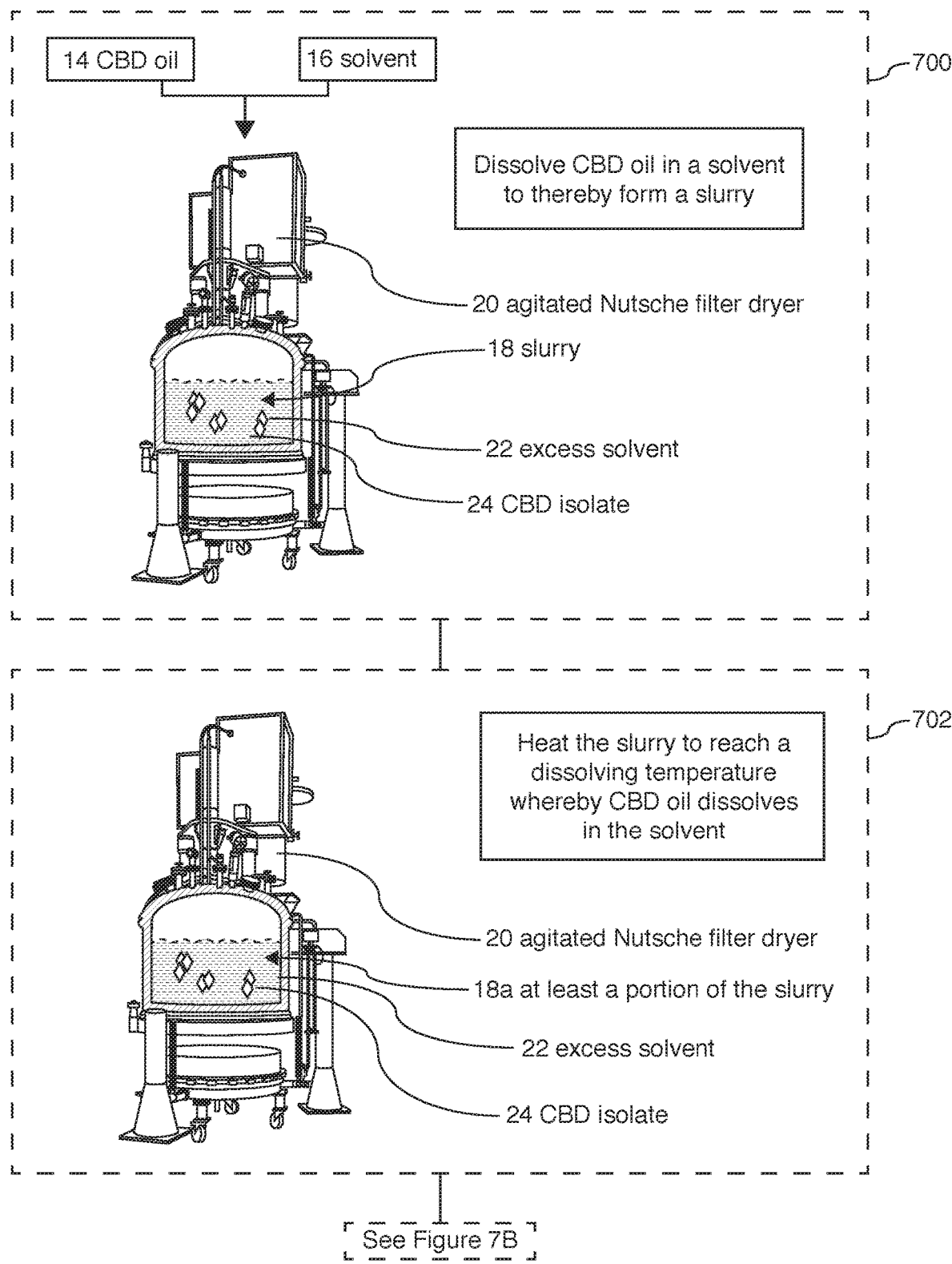
FIGS. 7A, 7B, and 7C illustrate a method of producing CBD isolate, according to some embodiments.
Figure 7B:
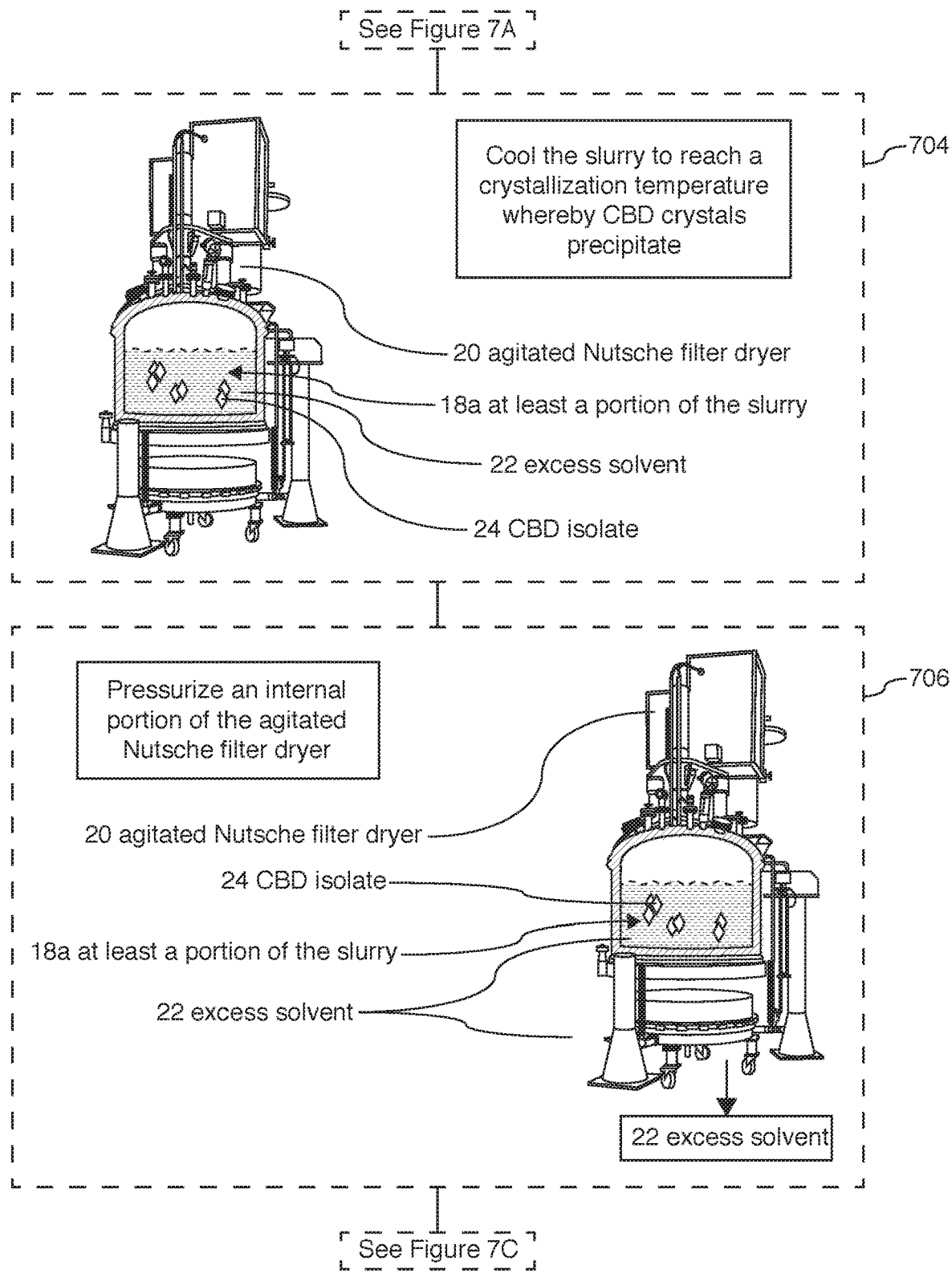
Figure 7C:
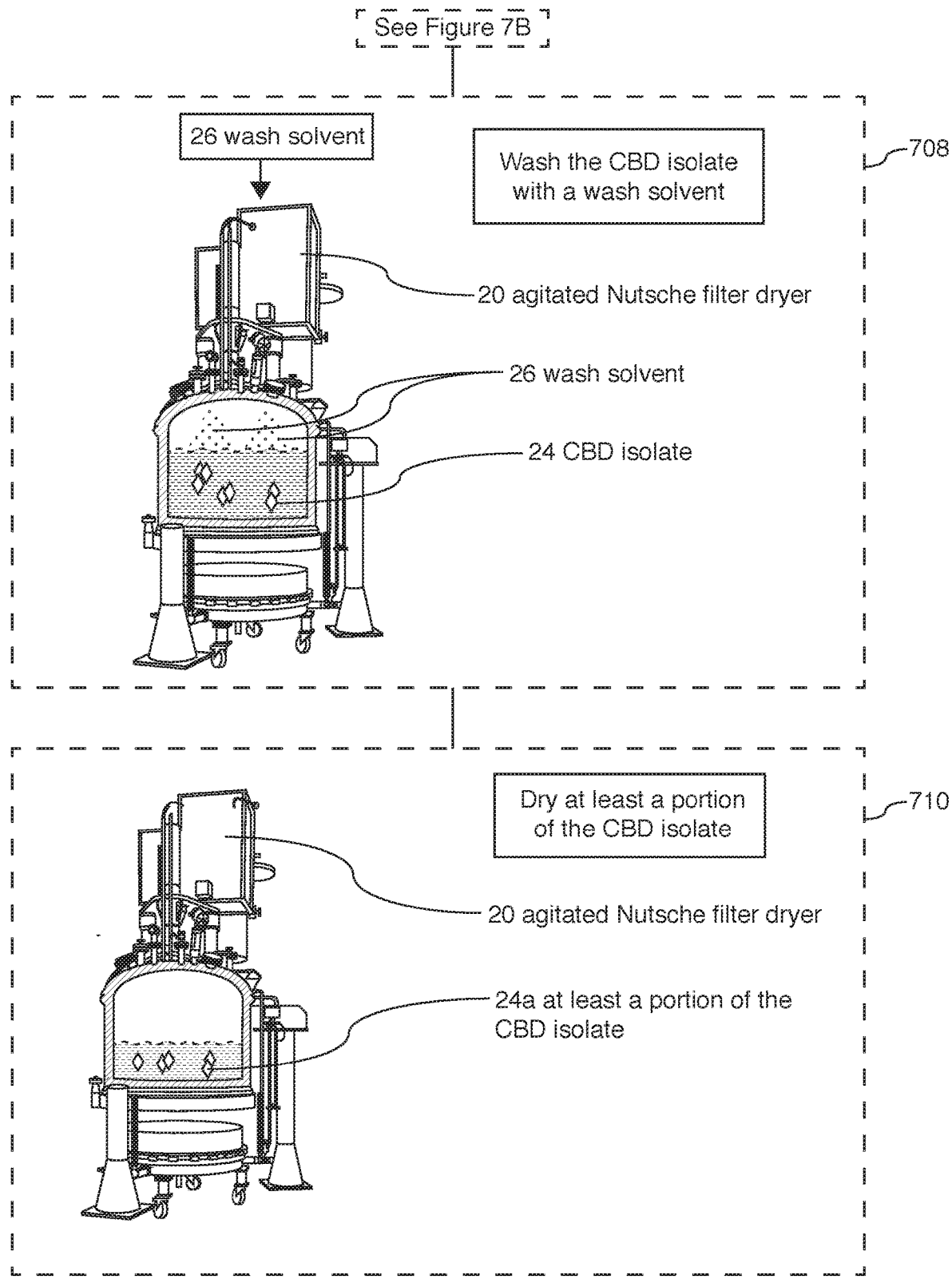

FIGS. 7A, 7B, and 7C illustrate a method of producing CBD isolate, according to some embodiments. FIG. 7A illustrates that, in some embodiments, the agitated Nutsche filter dryer 20 is jacketed and the dissolving step 700 is followed by heating, via the jacket of the agitated Nutsche filter dryer 20, the slurry 18 to reach a dissolving temperature whereby the CBD oil 14 dissolves in the solvent 16, shown in step 702. Similar to the heating step 404 discussed with reference to the system 10a, the dissolving temperature may define a temperature greater than or equal to about 40 degrees C. The dissolving temperature may vary based on any number of factors in the crystallization process, including the type of solvent 16 used, the amount of CBD oil 14 and solvent 16 used, the presence of impurities in the CBD oil 14, and various other factors. In some embodiments, the heating step 702 takes about 30 minutes to reach the dissolving temperature and ensure that the CBD oil 14 dissolves substantially completely in the solvent 16.

FIG. 7B demonstrates that, in some embodiments, following the heating step 702 the method further comprises cooling, via the jacket of the agitated Nutsche filter dryer 20, the slurry to reach a crystallization temperature whereby CBD crystals precipitate (at step 704). The jacket of the agitated Nutsche filter dryer 20 may be the same type of jacket as the jacket of the agitated vessel 12. In some embodiments, the jacket of the agitated Nutsche filter dryer 20 is different from the jacket of the agitated vessel 12. At least one of the heating and cooling may be achieved by liquid heating and/or cooling of the jacket, electrically heating and/or cooling the jacket, or any other appropriate method of heating and/or cooling. Other methods of heating/cooling may also be used, as discussed previously in this disclosure. In some embodiments, dissolving the CBD oil 14 in the solvent 16 is achieved through the use of a pre-warmed solvent 16. Such an embodiment may not require the heating step described in step 702 of FIG. 7A. The solvent 16 may be warmed in a manner similar to the heating step 702; i.e. through the use of a jacketed vessel containing the solvent 16.

Similar to the cooling step 406 discussed with reference to the system 10a, the crystallization temperature may define a temperature less than or equal to about −10 degrees C. The crystallization temperature may vary based on any number of factors in the crystallization process, including the type of solvent 16 used, the amount of CBD oil 14 and solvent 16 used, the presence of impurities in the CBD oil 14, and various other factors. In some embodiments, the cooling step 704 takes between about 30 minutes and 1 hour to reach the crystallization temperature and ensure that the CBD isolate 24 precipitates out of the slurry 18. FIG. 7B continues with step 706, which demonstrates the pressurizing step also shown in steps 602 and 702 of FIGS. 6 and 7A, respectively. FIG. 7C includes steps 708 and 710, which show the washing step and drying step, respectively. In some embodiments, step 708 is substantially the same as step 604, and step 710 is substantially the same as step 606. As discussed with reference to FIG. 7B, prior to the drying step 710 the method may further comprise collecting excess wash solvent 28. After the drying step 710, the method may comprise collecting the CBD isolate 24.

Though not shown, the method may further comprise agitating the agitated Nutsche filter dryer 20. Agitation may be achieved by stirring and/or mixing the slurry 18 within the agitated Nutsche filter dryer 20, and/or any other suitable form of agitation. Some forms of agitation, such as stirring and/or mixing the slurry 18, may be achieved through the use of an agitator within the agitated Nutsche filter dryer 20. Similar to the agitation discussed with reference to the system 10a, the agitation may occur at least partially simultaneously with at least one of the heating step 702 and the cooling step 704. In addition, both the dissolving step 700 and the drying step 710 may comprise agitating the agitated Nutsche filter dryer 20. The agitation may work continuously for constant mixing or may operate intermittently for periods of mixing and rest, as appropriate. In some embodiments, the method does not require agitation to successfully precipitate CBD isolate 24.

In many embodiments, the agitated vessel 12 (system 10a) and the agitated Nutsche filter dryer 20 (systems 10a and 10b) are sized and configured proportionally to one another according to the crystallization process volume.

Other components of the systems 10a, 10b, including the collection vessel 30, the fluid coupling mechanism, and the quantities of CBD oil 14, solvent 16, and wash solvent 26 may also be sized according to the crystallization process volume.

As previously mentioned, the fluid coupling mechanism may create a closed system for the CBD isolate production process. In addition to the fluid coupling mechanism, the systems 10a-b may include additional components for maintaining control over process parameters. For example, the agitated vessel 12 and the agitated Nutsche filter dryer 20 may comprise at least one of a cover(s) to protect the contents of the component and a control valve(s) to regulate the flow of contents between the components. The cover(s) may also aid in temperature regulation as a component of insulation for the agitated vessel 12 and the agitated Nutsche filter dryer 20. In some embodiments, the cover(s) is attached to at least one of the components with a hinge, allowing the cover(s) to be opened and closed. Alternatively, the cover(s) may be completely removable from at least one of the components. In some embodiments, the cover(s) includes an opening(s), such as a hole(s), to provide a connection(s) to the fluid coupling mechanism in order to facilitate the transfer of contents between components. In many embodiments, the control valve(s) opens and closes in response to an availability of the agitated Nutsche filter dryer 20. The agitated Nutsche filter dryer 20 may direct the control valve(s) of the agitated vessel 12 to open, thus releasing the slurry 18 from the agitated vessel 12 to the agitated Nutsche filter dryer 20 without manual intervention from a system user.

Various machinery components of the systems 10a and 10b, including the agitated vessel 12, the agitated Nutsche filter dryer 20, the fluid coupling mechanism, and the collection vessel 30 may comprise any suitable single or combination of materials such as metal, plastic, rubber, and/or glass. The proper material or combination of materials for each component may be determined by the role of the component in precipitating CBD isolate.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

Although certain embodiments and examples are disclosed above, inventive subject matter extends beyond the specifically disclosed embodiments to other alternative embodiments and/or uses, and to modifications and equivalents thereof. Thus, the scope of the claims appended hereto is not limited by any of the particular embodiments described above. The structures, systems, methods, and/or devices described herein may be embodied as integrated components or as separate components. Furthermore, various omissions, substitutions, and changes in the form of the methods and systems described herein may be made without departing from the spirit of the inventions disclosed herein.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy. Furthermore, the phrase "at least one of" may be used as a shorthand way of saying "and/or". In this regard, the phrase "at least one of" may mean the same thing as "and/or".

The term "about" is used to mean approximately, and is not intended as a limiting term. For example, the disclosure includes the phrase "the wash solvent 26 is a cold solvent and defines a temperature that is less than or equal to about −10 degrees C." and in this context, "about" is not intended to limit the temperature to exactly −10 degrees C. In this regard, the phrase "the wash solvent 26 is a cold solvent and defines a temperature that is less than or equal to about −10 degrees C." may be interpreted to mean that the temperature ranges between +/−5 degrees of the stated value, or −15 degrees C. to −5 degrees C. With respect to time, the term "about" may be intended to mean+/−5 minutes.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A method of producing cannabidiol (CBD) isolate, comprising:
    dissolving, via an agitated Nutsche filter dryer, CBD oil in a solvent to thereby form a slurry comprising CBD isolate and excess solvent; and
    pressurizing an internal portion of the agitated Nutsche filter dryer to remove the excess solvent and capture the CBD isolate in a filter of the agitated Nutsche filter dryer.

2. The method of claim 1, wherein the pressurizing comprises applying a vacuum to the internal portion of the agitated Nutsche filter dryer.

3. The method of claim 2, further comprising drying, via the agitated Nutsche filter dryer, at least a portion of the CBD isolate.

4. The method of claim 3, further comprising prior to the drying, washing the CBD isolate with a wash solvent.

5. The method of claim 1, further comprising heating, via a jacket of the agitated Nutsche filter dryer, the slurry.

6. The method of claim 1, further comprising cooling, via a jacket of the agitated Nutsche filter dryer, the slurry.

7. The method of claim 3, further comprising applying a vacuum to the internal portion of the agitated Nutsche filter dryer, wherein the drying occurs in response to applying the vacuum.

8. The method of claim 3, further comprising heating the internal portion of the agitated Nutsche filter dryer.

9. The method of claim 8, wherein the drying occurs further in response to the heating.

10. The method of claim 4, wherein the wash solvent defines a temperature that is less than or equal to −10 degrees C.

11. The method of claim 4, wherein the wash solvent is different from the solvent.

12. The method of claim 4, further comprising collecting excess wash solvent.

13. The method of claim 5, further comprising dissolving the solvent in response to the heating.

14. The method of claim 12, further comprising dissolving the solvent to a temperature greater than or equal to 40 degrees C.

15. The method of claim 6, further comprising precipitating the CBD isolate in response to the cooling.

16. The method of claim 1, wherein the solvent comprises pentane.

17. The method of claim 1, wherein the solvent comprises heptane.

18. The method of claim 1, further comprising collecting the CBD isolate in a collection vessel of the agitated Nutsche filter dryer.

19. The method of claim 1, further comprising pressurizing the internal portion of the agitated Nutsche filter dryer to a gauge pressure of up to 10 barg.

20. The method of claim 1, further comprising condensing, via a condenser of the agitated Nutsche filter dryer, the excess solvent.

21. The method of claim 20, further comprising collecting the excess solvent.

* * * * *